United States Patent [19]

Taylor

[11] Patent Number: 5,354,431
[45] Date of Patent: Oct. 11, 1994

[54] PLURAL STAGE DRYING AND PURIFICATION OF PROPYLENE OXIDE

[75] Inventor: Mark E. Taylor, Orange, Tex.

[73] Assignee: Texaco Chemical Company, White Plains, N.Y.

[21] Appl. No.: 125,276

[22] Filed: Sep. 23, 1993

[51] Int. Cl.$^5$ .................. B01D 3/40; C07D 301/32
[52] U.S. Cl. .................. 203/64; 203/70; 203/74; 203/75; 203/81; 203/82; 549/541
[58] Field of Search ............ 203/64, 70, 51, 74, 203/75, 81, 82, 14, 5; 549/541, 542

[56] References Cited

U.S. PATENT DOCUMENTS

| | | | |
|---|---|---|---|
| 3,338,800 | 8/1967 | Binning et al. | 203/70 |
| 3,464,897 | 9/1969 | Jubin | 203/70 |
| 3,578,568 | 5/1971 | Washall | 203/64 |
| 3,607,669 | 9/1971 | Jubin | 203/70 |
| 3,838,020 | 9/1974 | Kageyama et al. | 203/64 |
| 3,843,488 | 10/1974 | Schmidt et al. | 203/70 |
| 3,881,996 | 5/1975 | Schmidt | 203/70 |
| 5,000,825 | 3/1991 | Shih et al. | 203/64 |
| 5,129,996 | 7/1992 | Shih | 203/64 |
| 5,133,839 | 7/1992 | Shih | 203/64 |
| 5,262,017 | 11/1993 | Meyer et al. | 203/64 |

Primary Examiner—Wilbur Bascomb, Jr
Attorney, Agent, or Firm—Kenneth R. Priem; James L. Bailey; Carl G. Ries

[57] ABSTRACT

Crude propylene oxide is purified by a distillation process wherein it is (a) extractively distilled in a first column using a $C_2$ to $C_6$ alkylene glycol extractive distillation agent to form a first overhead fraction comprising propylene oxide, $C_5$-$C_7$ hydrocarbons, methanol, water and oxygen-containing impurities, (b) wherein the first overhead fraction is separated in a plurality of intermediate distillation columns to provide an intermediate propylene oxide overhead fraction consisting essentially of propylene oxide and water, and (c) the intermediate propylene oxide overhead fraction is charged to a final distillation column using a $C_2$ to $C_6$ alkylene glycol extractive distillation agent to form a final overhead fraction consisting essentially of propylene oxide.

21 Claims, 1 Drawing Sheet

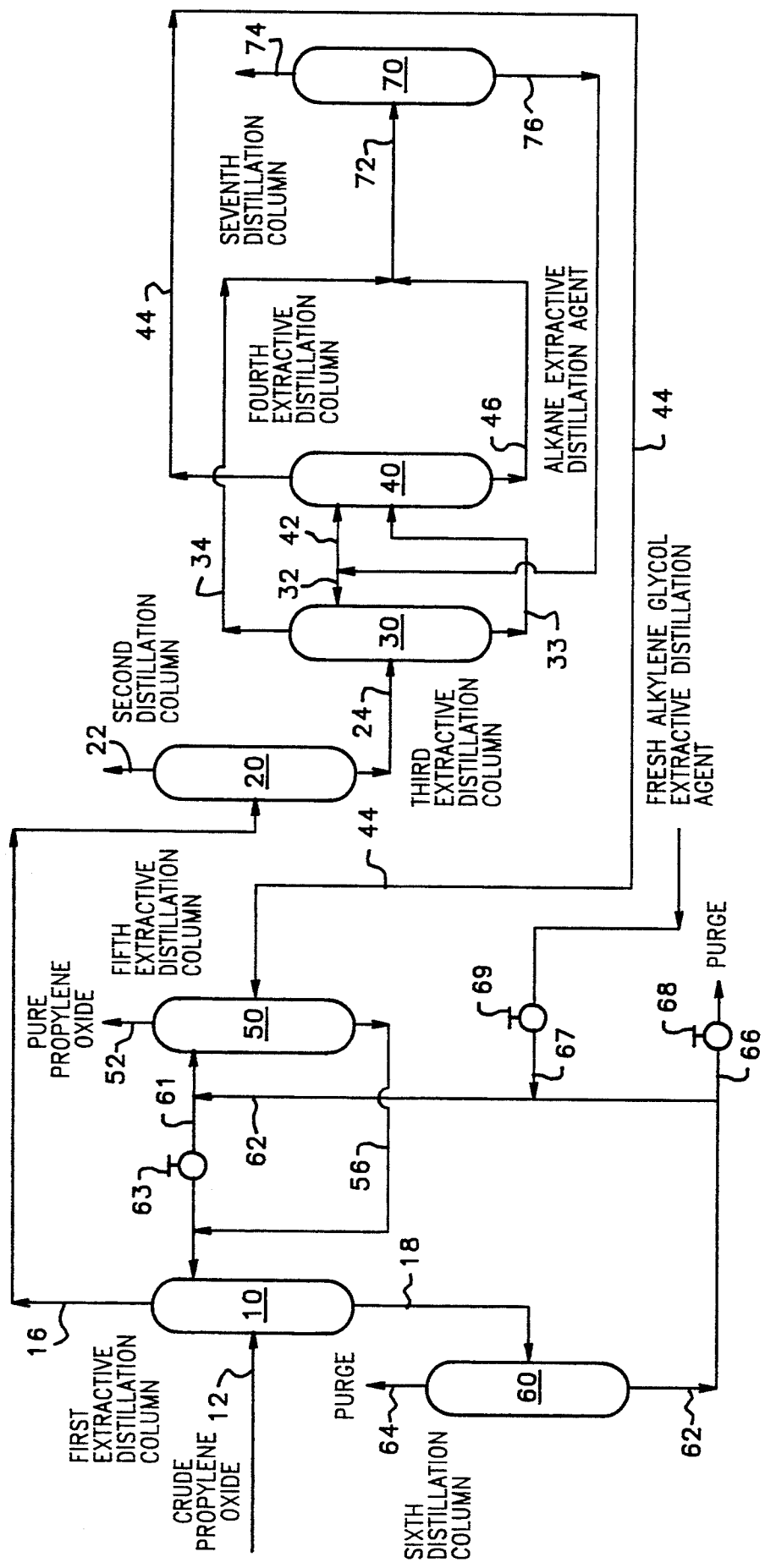

PLURAL STAGE DRYING AND PURIFICATION OF PROPYLENE OXIDE

BACKGROUND OF THE INVENTION

1. Field of the Invention

This invention relates to the plural stage drying and purification of propylene oxide. More particularly, this invention relates to a plural stage distillation process for removing contaminating quantities of impurities, including water, from propylene oxide. Still more particularly, this invention relates to a plural stage distillation process for the purification of impure propylene oxide contaminated with impurities including water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate. The impure propylene oxide is distilled by a plural stage process using a $C_2$ to $C_6$ alkylene glycol extractive distillation agent in a first drying stage and a terminal drying stage and a $C_7$ to $C_{10}$ alkane hydrocarbon extractive distillation agent for intermediate purification stages.

2. Prior Art

It is known to use alkane hydrocarbons containing 6 to 18 carbon atoms as extractive distillation agents in the purification of propylene oxide. See, for example, Binning et al. U.S. Pat. No. 3,338,800, Jubin U.S. Pat. No. 3,464,897, Jubin U.S. Pat. No. 3,607,669 and Scbmidt U.S. Pat. No. 3,843,488. Jubin U.S. Pat. No. 3,464,897 shows that an alkane such as octane is effective for the removal of 6 carbon atom alkane impurities such as 2-methyl pentane, 4-methyl pentene-1, 2-methyl pentene-1 and 2-methyl pentene-2. Schmidt U.S. Pat. No. 3,843,488 shows that alkanes containing from 8 to 20 carbon atoms, and preferably from 8 to 10 carbon atoms, such as n-octane, is effective for removing hydrocarbon impurities containing 5 to 7 hydrocarbons from propylene oxide.

It is also known to use alkylene glycols containing from 2 to 6 carbon atoms as extractive distillation agents in the purification of propylene oxide. See, for example, Washall U.S. Pat. No. 3,578,568, Kageyama et al. U.S. Pat. No. 3,838,020, Shih et al. U.S. Pat. No. 5,000,825, Marquis et al. U.S. Pat. No. 5,139,622, and Marquis et al. U.S. Pat. No. 5,160,587. Thus, Washall U.S. Pat. No. 3,578,568 discloses the use of ethylene glycol and propylene glycol as extractive agents for the purification of propylene oxide. Kageyama et al. U.S. Pat. No. 3,838,020 discloses the use of butylene glycols for this purpose. Shih et al. U.S. Pat. No. 5,000,825 discloses the use of glycols containing 2 to 4 carbon atoms such as ethylene glycol, propane diol, butane diol, etc. Marquis et al. U.S. Pat. No. 5,139,622 discloses the use of triethylene glycol as an extractive distillation agent and Marquis et al. U.S. Pat. No. 5,160,587 discloses the use of dipropylene glycol as an extractive distillation agent.

The use of plural stage distillation for the purification of propylene oxide has also been proposed.

Schmidt U.S. Pat. No. 3,881,996 discloses a plural stage process for the purification of propylene oxide including a first fractionation wherein light impurities such as acetaldehyde are removed overhead followed by a second distillation step wherein heavy impurities such as propionaldehyde are removed in order to provide a second distillate fraction which is then extractively distilled in the presence of octane in a third distillation zone to provide pure propylene oxide and to remove alkane hydrocarbon impurities such as $C_6$ carbon atom impurities from the propylene oxide. Schmidt et al. teach that it is important to use the proper sequence of distillation steps and that, for example, removal of heavy impurities such as propionaldehyde before the removal of light impurities such as acetaldehyde will lead to adverse results.

Shih U.S. Pat. No. 5,133,839 discloses a plural stage process for the purification of propylene oxide utilizing a conventional distillation zone which preferably contains two distillation columns, as in Schmidt U.S. Pat. No. 3,881,996, followed by extractive distillation of the parts of purified propylene oxide in two sequential extractive distillation columns using either isooctane or a lower alkylene glycol as the extractive distillation agent and removing lighter impurities in the first of the extractive distillation columns and heavier impurities from the second of the extractive distillation columns.

Meyer et al. U.S. Pat. No. 4,971,661 discloses a plural stage process for the purification of propylene oxide, but different extractive distillation agents such as water and acetone are used.

BACKGROUND INFORMATION

As illustrated by the prior art just discussed, it was known prior to the present invention to use plural stage distillation for the purification of propylene oxide and to use lower alkylene glycols and higher alkanes as extractive distillation agents. Thus, it was known that the use of the 8 to 10 carbon atom alkanes as extractive distillation agents was particularly effective for removing contaminating quantities of hydrocarbons such as hydrocarbons containing 6 to 7 carbon atoms from propylene oxide. It was also known to use the lower alkylene glycols, which are polar solvents, for the extractive distillation in order to remove water and oxygenated impurities.

It is known to substantially completely dehydrate propylene oxide using an extractive distillation agent such as a lower alkylene glycol. A relatively intractable problem is encountered with this technique because the distillation conditions necessary for the substantially complete dehydration of the propylene oxide are such that both that the extractive distillation agent and water tend to react with the propylene oxide increasing losses of both propylene oxide and the extractive distillation agent. It has been discovered in accordance with the present invention that this problem can be largely resolved by using a two-step drying process wherein in a first stage of a plural stage drying and purification process the crude, or impure, propylene oxide is partially dehydrated in a first drying stage using a $C_2$ to $C_6$ alkylene glycol extractive distillation agent, wherein other impurities are removed in intermediate stages utilizing a $C_8$ to $C_{10}$ alkane hydrocarbon extractive distillation agent and wherein final dehydration drying is accomplished in a terminal drying step again using a $C_2$ to $C_6$ alkylene glycol extractive distillation agent. With this technique, the distillation conditions utilized in the first drying step and the last drying step can be significantly less vigorous than those normally required for the complete dehydration of propylene oxide.

Thus, as is pointed out, for example by Schmidt U.S. Pat. No. 3,881,996, the sequence of distillation steps employed in the plural stage purification of propylene oxide is crucial to effective purification. Reversing or otherwise altering the sequence of steps can lead to adverse results.

Pentanes and pentenes are present in crude propylene oxide as minor impurities. The removal of pentanes and pentenes presents a difficult problem.

Thus, when partially purified propylene oxide containing contaminating quantities of 5 to 7 carbon atom hydrocarbons such as pentanes, pentenes, hexanes, hexenes, heptanes and heptenes is subjected to extractive distillation using an $C_8$–$C_{10}$ alkane hydrocarbon extractive distillation agent such as octane, a significant portion of the pentanes and pentenes will remain with the overhead purified propylene oxide rather than being removed therefrom for withdrawal from the bottom of the tower together with the extractive distillation agent and the other impurities.

Pentanes, isopentane and pentenes may be removed like other hydrocarbon impurities by using a $C_8$–$C_{10}$ alkane in an extractive distillation. The $C_8$–$C_{10}$ alkane solvent lowers the relative volatility of the hydrocarbons relative to propylene oxide. However, the degree of relative volatility change is proportional to the amount of solvent present. A more economical and efficient means of removing pentanes and pentenes is by a distillation upstream of the $C_8$–$C_{10}$ alkane extractive distillation. The C5 stripper tower should not be located downstream of the $C_8$–$C_{10}$ extractive distillation since the final PO product would then be a bottoms product off the stripper. It is advantageous to take high purity products off the top of columns rather than off the bottom.

In accordance with the present invention, partial drying of the propylene oxide and substantially complete removal of the $C_5$ hydrocarbons is accomplished in the first stage of the plural distillation process utilizing a $C_2$–$C_6$ alkylene glycol extractive distillation agent.

SUMMARY OF THE INVENTION

In accordance with the present invention, crude propylene oxide is separated from contaminating quantities of water, hexanes, hexenes, pentanes, pentenes, and oxygen-containing impurities by a sequential extractive distillation process wherein the crude propylene oxide is first extractively distilled using a lower alkylene glycol extractive distillation agent to form a first partially dehydrated overhead fraction comprising propylene oxide, water, hexanes, hexenes, pentanes and pentenes and oxygen-containing impurities boiling above propylene oxide, wherein the first overhead distillation fraction is separated in a second distillation column into a second overhead distillation fraction comprising most of the pentanes, pentenes, oxygen-containing impurities boiling above propylene oxide and a residual amount of propylene oxide and a second partially purified propylene oxide bottoms fraction comprising propylene oxide, water, hexenes, hexanes and only residual quantities of pentenes and pentanes, wherein the partially purified second bottoms fraction is extractively distilled in a third distillation column using a $C_8$–$C_{10}$ alkane hydrocarbon extractive distillation agent to provide a third further purified bottoms fraction containing substantially all of the propylene oxide, hexenes, hexanes and pentenes charged to the third distillation column, wherein the third further purified propylene oxide bottoms fraction is additionally purified in a fourth extractive distillation column using a $C_8$–$C_{10}$ alkane hydrocarbon extractive distillation agent to provide a fourth propylene oxide overhead fraction consisting essentially of propylene oxide and water. The propylene oxide overhead fraction consisting essentially of propylene oxide and water is charged to a terminal distillation stage where it is dehydrated utilizing an extractive distillation agent consisting essentially of a $C_2$ to $C_6$ alkylene glycol extractive distillation agent to provide a final overhead distillate fraction consisting essentially of anhydrous purified propylene oxide.

In accordance with a preferred embodiment of the present invention, impure propylene oxide contaminated with water, pentanes, pentenes, hexenes, hexanes and oxygen-containing impurities is purified by a sequential extractive distillation process wherein (a) the impure propylene oxide is extractively distilled using a first $C_2$ to $C_6$ alkylene glycol extractive distillation agent to form a first lighter distillation fraction containing all of the propylene oxide, less than 50 wt. % of the water, hexenes, hexanes, pentenes and pentanes and oxygen-containing impurities boiling above propylene oxide and a first heavier distillation fraction containing more than 50 wt. % of the water and oxygen-containing impurities boiling above propylene oxide, including acetone, tertiary butyl alcohol, methanol and isopropyl alcohol, and all of the first extractive distillation agent, wherein (b) the first lighter distillation fraction is separated in a second distillation column into a second lighter distillation fraction containing the pentanes, pentenes, oxygen-containing impurities boiling above propylene oxide, including acetaldehyde, and a residual amount of propylene oxide and a second heavier partially purified distillation fraction containing substantially all of the propylene oxide, water, hexenes, hexanes charged to the second distillation column, wherein (c) the second heavier partially purified distillation fraction is extractively distilled in a third distillation column using a $C_8$ to $C_{10}$ alkane hydrocarbon extractive distillation agent to provide a third lighter distillation fraction containing residual oxygen-containing impurities, including methyl formate, acetaldehyde and methanol, and more than half of the water charged to the third distillation column and water and a third heavier further purified distillation fraction containing substantially all of the propylene oxide, hexenes, hexanes and less than half of the water charged to the third distillation column, wherein (d) the third heavier further purified distillation fraction is extractively distilled using a $C_8$ to $C_{10}$ alkane extractive distillation agent to provide a fourth lighter distillation fraction consisting essentially of water and propylene oxide and a fourth heavier distillation fraction containing all of the extractive distillation agent, all the hexenes, hexanes and also residual quantities of propylene oxide, and wherein (e) the fourth lighter distillation fraction is charged to a fifth terminal distillation column where it is extractively distilled using a $C_2$ to $C_6$ alkylene glycol extractive distillation agent to form a fifth lighter substantially anhydrous distillation fraction containing substantially all of the propylene oxide charged to the fifth distillation column and a fifth bottoms fraction comprising the extractive distillation agent, water, and residual propylene oxide.

In accordance with the preferred embodiment of the present invention, a distillation process is provided for the purification of crude propylene oxide contaminated with water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate comprising the steps of:

a. Charging the crude propylene oxide to a first extractive distillation column;
b. Charging a lower alkylene glycol extractive distillation agent to the first extractive distillation column at a feed point above the point of introduction of the impure propylene oxide;
c. Fractionating the crude propylene oxide in the first extractive distillation column under distillation conditions selected to provide a first lighter distillation fraction containing substantially all of the propylene oxide, propylene, propane, acetaldehyde, methyl formate, hexenes, hexanes, pentenes and pentanes and a portion of the methanol and water and also a first heavier distillation fraction containing substantially all of the propionaldehyde, acetone, t-butyl alcohol, t-butyl formate, isopropyl alcohol and the remainder of the methanol and water and all of the extractive distillation agent;
d. Charging a second feedstock comprising the first lighter distillation fraction to a second distillation column;
e. Fractionating the second feedstock in the second distillation column under distillation conditions selected to provide a second lighter distillation fraction containing substantially all of the propylene, propane, acetaldehyde, pentanes, pentenes and a residual amount of propylene oxide and a second heavier partially purified distillation fraction containing substantially all of the propylene oxide, water, hexenes and hexanes;
f. Charging a third feedstock comprising the second heavier distillation fraction to a third extractive distillation column;
g. Charging a $C_8$ to $C_{10}$ alkane hydrocarbon extractive distillation agent to the third extractive distillation column at a feed point above the point of introduction of the third feedstock;
h. Fractionating the third feedstock in the third extractive distillation column under distillation conditions selected to provide a third lighter distillation fraction containing water, substantially all of the acetaldehyde, methyl formate, methanol and residual quantities of propylene oxide and extractive distillation agent and a third further purified heavier distillation fraction containing substantially all of the propylene oxide, water and hexanes charged to the third distillation column;
i. Charging a fourth feedstock comprising the third heavier distillation fraction to a fourth extractive distillation column;
j. Charging a $C_8$ to $C_{10}$ alkane hydrocarbon extractive distillation agent to the fourth extractive distillation column at a feed point above the point of introduction of the third feedstock;
k. Fractionating said fourth feedstock in the fourth extractive distillation column under distillation conditions selected to provide a fourth additionally purified lighter intermediate distillation fraction consisting essentially of water and propylene oxide, and a fourth heavier distillation fraction containing substantially all of the extractive distillation agent, hexenes and hexanes and also residual quantities of propylene oxide;
l. Charging a fifth feedstock comprising the fourth lighter distillation fraction to a fifth terminal extractive distillation column;
m. Charging a lower alkylene glycol extractive distillation agent to the fifth extractive distillation column at a feedpoint above the point of introduction of the fifth feedstock; and
n. Fractionating said fifth feedstock in said fifth extractive distillation column under distillation conditions selected to provide a fifth lighter distillation fraction consisting essentially of propylene oxide and a fifth heavier distillation fraction containing residual propylene oxide and substantially all of the water and extractive distillation agent charged to the fifth distillation column.

BRIEF DESCRIPTION OF THE DRAWING

The drawing is a schematic flow sheet with conventional parts omitted showing the general recovery sequence that is used in accordance with the present invention to purify propylene oxide.

DESCRIPTION OF THE PREFERRED EMBODIMENT

Turning now to the drawing, there is shown a schematic flow sheet illustrating a preferred method for practicing the process of the present invention. In the drawing, conventional parts such as valves, pumps, temperature sensors, pressure sensors, heaters, coolers, flow control regulation apparatus, reboilers, reflux condensers, etc., have been omitted.

The crude or impure propylene oxide to be purified in accordance with the present invention is typically propylene oxide prepared by the reaction of tertiary butyl hydroperoxide with propylene in the presence of a molybdenum catalyst to provide a reaction mixture comprising unreacted propylene, unreacted tertiary butyl hydroperoxide, tertiary butyl alcohol, propylene oxide, and impurities. This reaction product is separated in a distillation zone (not shown) into a plurality of fractions including a propylene recycle fraction, a crude propylene oxide fraction, a tertiary butyl alcohol fraction and a residue fraction.

The crude propylene oxide obtained in this fashion is suitably used as a feedstock for the present invention and will normally be contaminated with impurities including water, propylene, propane, acetaldehyde, methyl formate, propionaldehyde, hexenes, acetone, hexanes, methanol, tertiary butyl alcohol, pentane, isopentane, pentenes, isopropyl alcohol and tertiary butyl formate.

The impure propylene oxide will normally contain from about 97 to about 99 wt. % of propylene oxide, the balance being impurities such as those enumerated above. It will be understood that some of the enumerated impurities will not always be present in impure propylene oxide and that other impurities not listed may be present in minor quantities. The impurities, broadly speaking, comprise water, hydrocarbons such as propylene, propane, hexenes, hexanes, pentane, isopentane and pentenes, and oxygenated impurities including aldehydes, alcohols, esters, etc. The hydrocarbon impurities will normally contain from about 2 to about 6 carbon atoms and the oxygenated impurities will normally contain from about 1 to about 6 carbon atoms also.

In accordance with the present invention, a crude propylene oxide of the type described is charged to a first extractive distillation column 10 by way of a charge line 12. The fractional distillation column 10 may suitably comprise from about 40 to about 80 theoretical trays and the charge line 12 for the impure propylene oxide will normally be at least about 10 to about 30 trays from the bottom of the distillation tower.

For example, the impure propylene oxide, which will suitably comprise about 98.5 wt. % propylene oxide, the balance being impurities as mentioned above, may be charged at a temperature of about 100° F. to about 160° F.

An alkylene glycol extractive distillation agent is also charged to the line 10 by a line 56. The alkylene glycol extractive distillation agent suitably may be an alkylene glycol containing from 2 to 6 carbon atoms such as ethylene glycol, propylene glycol, 1,4-propane diol, 1,3-2-methyl propane diol, 1,4-butane diol, 2-methyl-1,3-propane diol, diethylene glycol, triethylene glycol, dipropylene glycol, etc. Preferred extractive distillation agents include triethylene glycol and dipropylene glycol.

The alkylene glycol extractive agent 56 will suitably be charged to the extractive distillation column 10 in the ratio of about 2 to 7 parts of crude propylene oxide per part of alkylene glycol extractive distillation agent.

Extractive distillation conditions are adjusted in the extractive distillation tower 10 so as to provide for the recovery as overhead or as a distillate fraction 16 of substantially all of the propylene oxide charged to the extractive distillation column 10.

The temperature at the bottom of the extractive distillation column 10 may suitably be about 300°–400° F. and the pressure may be about 20–50 psia. The temperature at the top of the extractive distillation column 10 may, for example, be about 80°–120° F. and the pressure may suitably be about 15–25 psia. A first lighter distillation fraction comprising impure propylene oxide is removed from the column 10 by way of a line 16 and may suitably comprise more than 99 wt. % propylene oxide, the balance being impurities including acetaldehyde, methyl formate, hexenes, hexanes, methanol, water, pentanes, isopentanes and pentenes. A heavier distillation fraction 18 discharged adjacent the bottom of the extractive distillation column 10 will comprise the alkylene glycol extractive distillation agent and impurities including water, propionaldehyde, acetone, methanol, tertiary butyl alcohol, isopropyl alcohol, tertiary butyl formate and the alkylene glycol extractive distillation agent.

A second feedstock comprising the first lighter distillation fraction 16 is charged to a second distillation column 20 which may suitably contain from about 20 to about 40 theoretical trays, the second feedstock being suitably charged to about 8 to about 16 theoretical trays from the bottom of the tower. Distillation conditions are adjusted in the distillation column 20 to provide a second lighter distillation fraction discharged by way of a line 22 and a second heavier partially purified distillation fraction discharged by a line 24. Distillation conditions are suitably adjusted in the distillation column 20 so that substantially all of the propylene oxide will be present in the second heavier distillation fraction 24. Typically, the lighter distillation fraction 22 will comprise impurities including propylene, propane, acetaldehyde and, significantly, substantially all of the pentanes and pentenes charged to the distillation column 20. The second heavier distillation fraction 24 will typically contain heavier oxygen-containing impurities, water, substantially all of the propylene oxide, hexenes and hexanes.

A third feedstock comprising the second heavier distillation fraction 24 is charged to a third distillation column 30 together with a $C_8$ to $C_{10}$ alkane hydrocarbon extractive distillation agent which is charged by a line 32.

The alkane extractive distillation agent may suitably be charged to the third distillation column 30 in the ratio of about 5 to about 7 parts of extractive distillation agent per part of third feedstock 24. Extractive distillation conditions are adjusted in the distillation column 30 to provide for a fourth heavier distillation fraction 33 containing water, substantially all of the propylene oxide, hexenes and hexanes and a lighter distillation fraction 34 which will typically comprise impurities such as methyl formate, acetaldehyde, water and methanol. Residual quantities of propylene oxide and hexane may also be present.

The extractive distillation agent charged to the distillation column 30 is suitably an 8–10 carbon atom alkane such as normal octane or isooctane. The third feedstock 24 charged to the third distillation column 30 may be suitably charged at a temperature of about 130°–180° F. The temperature at the bottom of the extractive distillation column 30 may suitably be about 180°–220° F. and the pressure may suitably be about 30–50 psia. The temperature adjacent the top of the extractive distillation tower 30 may suitably be about 130°–160° F. and the pressure may suitably be about 20–40 psia.

A fourth feedstock comprising the third heavier distillation fraction 33 is charged to a fourth extractive distillation tower 40 together with an alkane extractive distillation agent such as a $C_8$ to $C_{10}$ alkane which is charged by way of a line 42. The extractive distillation agent 42 may be charged to the extractive distillation column 40 in the ratio of about 0.4 to about 0.8 parts of extractive distillation agent per part of fourth feedstock 33.

Distillation conditions are adjusted in the distillation column 40 to provide lighter distillation fraction 44 consisting essentially of water and propylene oxide and a heavier distillation fraction 46 comprising the hexenes, hexanes and the extractive distillation agent.

Suitably, the temperature at the top of the distillation column 40 may be about 100°–130° F. and the pressure may be about 10–30 psia. The temperature adjacent the bottom of the distillation column 40 may suitably be about 250°–290° F. and the pressure may suitably be about 25–45 psia.

A fifth feedstock comprising the fourth lighter distillation fraction 44 is charged to a fifth (terminal) extractive distillation tower 50 together with a $C_2$ to $C_6$ alkylene glycol extractive distillation agent which is charged by a line 62.

The alkylene glycol extractive distillation agent 62 will suitably be charged to the extractive distillation column 50 in the ratio of about 4 to about 6 parts of the fifth feedstock 44 per part of alkylene glycol extractive distillation agent.

Extractive distillation conditions are adjusted in the extractive column 50 so as to provide for the recovery of a lighter distillate fraction 52 consisting essentially of propylene oxide and substantially completely free from water.

The temperature at the bottom of extractive distillation column 50 may suitably be from about 180° to about 220° F. and the pressure may be from about 20 to about 50 psia. The temperature at the top of the extractive distillation column 50 may, for example, be within the range of about 85° to 120° F. and the pressure may suitably be from about 15 to 25 psia. A heavier distillation fraction 56 discharged from adjacent the bottom of extractive distillation column 50 will comprise water, the alkylene glycol extractive distillation agent, and propylene oxide. The fifth distillation column 50 may suitably comprise about 10 to about 40 theoretical trays and the charge line 44 will suitably be at least about 5 to about 20 trays from the bottom of the distillation tower 50.

By operating the fifth distillation column under distillation conditions such that about 5 to about 20 wt. % of propylene oxide is present in the heavier distillation fraction 56, it is possible to obtain complete dewatering of propylene oxide discharged by the line 52 under distillation conditions that are mild enough to substantially inhibit reaction of propylene oxide with water and the extractive distillation agent.

In accordance with a preferred embodiment of the present invention, the heavier distillation fraction 56, which comprises the alkyl glycol extractive distillation agent and propylene oxide is charged to the first distillation column 10 in order to provide for the extractive distillation agent required therein and in order that the propylene oxide contained therein may be recovered by overhead line 16.

A sixth feedstock comprising the first heavier distillation fraction 18 from the first distillation column 10 may be charged to a sixth distillation column 60 containing from about 20 to about 60 theoretical trays wherein the sixth feedstock may be separated under distillation conditions adjusted to provide for the recovery of substantially all of the alkylene glycol extractive distillation agent as a heavier distillation fraction discharged from the distillation column 60 by a line 62 and a lighter distillation fraction 64 discharged from the distillation column 60 and containing propylene oxide, water, acetone, tertiary butyl alcohol, methanol and isopropyl alcohol, which is preferably purged from the system.

The pressure at the top of the sixth distillation column 50 may suitably be about 0.1–1.0 psia and the temperature may suitably be about 90°–130° F. The pressure at the bottom of the distillation column 60 may suitably be about 0.1–1.1 psia and the temperature may suitably be about 300°–400° F.

In accordance with a preferred embodiment of the present invention, the heavier distillation fraction 62, which comprises the alkylene glycol extractive distillation agent is charged to the fifth distillation column 50 in order to provide for the extractive distillation agent required therein. If desired, a portion of the alkylene glycol extractive distillation agent in the line 62 may be routed by a branch line 61 controlled by a valve 63 to the extractive distillation charge line 56 for the first extractive distillation column 10. If contaminants build up in the heavier distillation fraction 62, a portion of the fraction 62 may be purged from the system by a branch purge line 66 controlled by a valve 68. Fresh alkylene glycol extractive distillation agent may be added to the system, as needed, by a charge line 67 controlled by a valve 69 that is located downstream from the purge line 66.

A seventh feedstock comprising the third lighter distillation fraction 34 and the fourth heavier distillation fraction 46 may suitably be charged by way of a line 72 to a seventh distillation column 70 which may comprise, for example, from about 30 to about 50 theoretical trays and wherein the seventh feedstock is introduced at least about 20 theoretical trays from the bottom of the column. Distillation conditions are adjusted within the distillation column 70 to provide for the recovery of a seventh lighter distillation fraction 74 comprising acetaldehyde, methyl formate, propylene oxide, hexenes, methanol and a minor Mount of $C_8$ to $C_{10}$ alkane and a sixth heavier distillation fraction 76 comprising substantially all of the $C_8$ to $C_{10}$ alkane extractive distillation agent charged to the distillation column 70 by the line 72. For example, the distillation conditions established in the sixth distillation column 60 may include a pressure at the top of the column of about 15–30 psia and a temperature of about 100°–140° F. and a pressure at the bottom of the column of about 20–40 psia and a temperature of about 200°–300° F. The $C_8$–$C_{10}$ extractive distillation agent in line 76 may be recycled to extractive distillation charge lines 32 and 42 for columns 30 and 40, respectively.

EXAMPLES

The invention will be further illustrated by the following specific example which is given by way of illustration and not as a limitation on the scope of this invention. Where parts are mentioned, they are parts by weight.

About 1000 parts of an impure propylene oxide feedstock 12 containing about 98.5 wt. % of propylene oxide and contaminated with impurities including water, propylene, propane, acetaldehyde, methyl formate, propionaldehyde, hexenes, acetone, hexanes, methanol, t-butyl alcohol, n-pentane, isopentane (i.e., 2-methyl butane), pentene, isopropyl alcohol and tertiary butyl formate are separated under the extractive distillation conditions in a distillation column 10 in the presence of a triethylene glycol extractive distillation agent into a first lighter distillation fraction 16 (about 986 parts) containing about 99 wt. % of propylene oxide and about 1 wt. % of contaminants including water, propylene, propane, acetaldehyde, methyl formate, hexenes, hexanes, pentenes, pentanes and methanol and a first heavier distillation fraction 18 containing water, propionaldehyde, acetone, tertiary butyl alcohol, tertiary butyl formate, isopropyl alcohol, methanol and the triethylene glycol extractive distillation agent. The first heavier distillation fraction 18 is separated in sixth distillation column 60 into a heavier fraction 62 comprising the triethylene glycol extractive distillation agent which is charged to the extractive distillation column 50 and a lighter overhead fraction 64 comprising propylene oxide, water, acetone, tertiary butyl alcohol, methanol and isopropyl alcohol that is discharged from the system.

A second feedstock comprising the lighter distillation fraction 16 is separated in the second distillation column 20 into about 1005 parts of a heavier distillation fraction 24 and about 1 part of a lighter distillation fraction 22 containing propylene, propane, acetaldehyde, pentenes and pentanes charged to the extractive distillation column 10 by the line 12.

The second heavier distillation fraction 24 discharged from the distillation column 20 will comprise substantially all of the propylene oxide, water, hexenes and hexanes and heavier oxygen-containing impurities. This fraction is charged by way of the line 24 to a third distillation column 30 together with about 5620 parts of octane charged to the distillation column 30 by a line 32. The distillation column 30 is operated in the manner described above to provide a lighter distillation fraction 34 (about 1 part) and a heavier distillation fraction 33 (about 6624 parts). The fraction 34 will comprise acetaldehyde, methyl formate, methanol, water and residual quantities of propylene oxide and octane. The third heavier distillation fraction 33 will comprise propylene oxide, water and substantially all of the octane charged to the third distillation column 30.

A fourth feedstock comprising a third heavier distillation fraction 33 is charged to the fourth extractive distillation column 40 where it is separated together with about 3690 parts of octane in the manner described above into about 1005 parts of an overhead distillation fraction consisting essentially of propylene oxide and water. A heavier distillation fraction 46 discharged from the column 40 will comprise about 9309 parts of octane, hexenes, hexanes and residual quantities of propylene oxide.

A fifth feedstock comprising the fourth lighter distillation fraction 44 (about 1005 parts) together with about 180 parts of triethylene glycol is charged to the column 50 by the line 56. The fifth feedstock is separated in the fifth distillation column 50 into a fifth lighter overhead distillation fraction consisting essentially of propylene oxide (about 965 parts) and a fifth heavier distillation fraction 54 comprising about 180 parts of triethylene glycol, 20 parts propylene oxide and water. The fifth heavier distillation fraction 54 is charged to first distillation column 10 to provide the extractive distillation required therein and to provide for recovery of the propylene oxide contained therein.

The residual $C_8$ to $C_{10}$ alkane hydrocarbon extractive distillation agent discharged from the column 30 by the line 34 and the $C_8$ to $C_{10}$ alkane hydrocarbon discharged from the column 40 by the line 46 may be charged by line 72 to seventh distillation column 70 where it is resolved into a lighter distillation fraction 74 comprising impurities and a heavier distillation fraction 76 comprising the $C_8$–$C_{10}$ alkane distillation agent which is recycled through the distillation columns 30 and 40 by extractive distillation charge lines 32 and 42, respectively.

As a further example, a computer simulation of the distillation column 50 was conducted using a feedstock consisting essentially of propylene oxide contaminated with about 0.005 wt. % of water. In the simulation, propylene oxide feed was charged to the distillation column 50 through the line 44 at the rate of about 10,000 #/hr at a temperature of about 110° F. and a pressure of about 95 psia. Triethylene glycol was charged by way of line 62 at the rate of about 2,000 #/hr at a temperature of about 114° F. and a pressure of about 95 psia. The column 50 was operated at a pressure of about 25 psia, a bottom temperature of about 200° F., a top temperature of about 100° F. and a feedstock ratio of about 1:1.

About 9,825 #/hr of propylene oxide was withdrawn from adjacent the top of the column 50 by line 52 together with only about 0.5 #/hr of water. A higher boiling fraction was withdrawn by line 54 adjacent the bottom of the column 50 at the rate of about 2,000 #/hr of triethylene glycol, about 174 #/hr of propylene oxide and about 0.55 pounds per hour of water. Thus, the distillate propylene oxide product 52 is contaminated with only about 0.0005 wt. % of water and there is a combined substantially quantitative recovery of propylene oxide, demonstrating a substantially complete recovery of propylene oxide without noticeable degradation of the propylene oxide.

Having thus described my invention, what is claimed is:

1. A method for the purification of crude propylene oxide contaminated with minor amounts of water, $C_5$ and $C_6$ hydrocarbons and oxygen-containing impurities which comprises the steps of:

extractively distilling said crude propylene oxide in the presence of a $C_2$ to $C_6$ alkylene glycol extractive distillation agent in a first extractive distillation zone under extractive distillation conditions selected to provide a first lighter distillation fraction comprising propylene oxide, water and said hydrocarbon and said oxygen-containing impurities and a first heavier distillation fraction comprising said extractive distillation agent and a portion of the water present in the crude propylene oxide;

distilling said first lighter distillation fraction in a second distillation column, a third extractive distillation column and a fourth extractive distillation column in the presence of a $C_8$ to $C_{10}$ alkane hydrocarbon extractive distillation agent under distillation conditions selected to remove said hydrocarbon and oxygen-containing impurities and to provide a fourth distillation fraction consisting essentially of propylene oxide and a minor amount of water; and extractively distilling said fourth fraction in a fifth distillation column in the presence of a $C_2$ to $C_6$ alkylene glycol extractive distillation agent under distillation conditions selected to provide a final fifth lighter distillation fraction consisting essentially of dehydrated propylene oxide and a final fifth heavier distillation fraction comprising said extractive distillation agent, water and a minor amount of propylene oxide.

2. A method as in claim 1 wherein the heavier final fifth distillation fraction is recycled to said first extractive distillation column.

3. A method as in claim 1 wherein the distillation conditions in the first extractive distillation column include a bottoms temperature of about 300° to 400° F., a bottoms pressure of about 20 to 50 psia, a temperature adjacent the top of the first extractive distillation column of about 80° to about 120° F., a pressure adjacent the top of the first extractive distillation column of about 15 to 25 psia and a ratio of crude propylene oxide to said $C_2$ to $C_6$ alkylene glycol extractive distillation agent of about 2 to 7, and wherein the distillation conditions in said fifth distillation column include a temperature adjacent the bottom of said fifth distillation column of about 200° to 220° F., a pressure adjacent the bottom of said fifth distillation column of about 20 to 50 psia, a temperature adjacent the top of said fifth distillation column of about 85° to 120° F., a pressure adjacent the top of said fifth distillation column of about 15 to 25 psia and a ratio of said second heavier distillation fraction to said $C_2$ to $C_6$ alkylene glycol extractive distillation agent of about 4 to 6.

4. A process for separating contaminating quantities of hexenes, hexanes, pentenes, pentanes, water and oxygen-containing impurities from impure propylene oxide which comprises:

extractively distilling the impure propylene oxide in a first distillation column using a $C_2$ to $C_6$ alkylene glycol extractive distillation agent to form a first lighter fraction comprising propylene oxide, hexenes, hexanes, pentenes, pentanes, water, methanol and oxygen-containing impurities boiling above propylene oxide and a first heavier distillation fraction comprising said alkylene glycol extractive distillation agent and impurities;

fractionating the first lighter fraction in a second distillation column to obtain a second lighter fraction comprising essentially all of the pentanes and pentenes and most of the oxygen-containing impurities boiling above propylene oxide and a partially purified second heavier propylene oxide fraction comprising propylene oxide, water, hexenes and hexanes;

extractively distilling the partially purified second heavier fraction in a third distillation column using a $C_8$ to $C_{10}$ alkane hydrocarbon extractive distillation agent to provide a third further purified heavier bottoms third fraction comprising substantially all of the propylene oxide, water, hexenes and hexanes charged to the third distillation column;

extractively distilling the further purified third heavier fraction in a fourth distillation column using a $C_8$ to $C_{10}$ alkane hydrocarbon extractive distillation agent to provide an additionally purified fourth propylene oxide lighter fraction consisting essentially of water and propylene oxide free of said contaminants; and extractively distilling the fourth lighter propylene oxide fraction in a fifth terminal distillation column using a $C_2$ to $C_6$ alkylene glycol extractive distillation agent to form a fifth lighter fraction consisting essentially of propylene oxide.

5. A distillation process for the purification of impure propylene oxide feedstock contaminated with hexenes, hexanes, pentanes, pentenes, water, methanol and oxygen-containing impurities which comprises the steps of:

separately charging said impure propylene oxide feedstock and a $C_2$ to $C_6$ alkylene glycol extractive distillation agent to a first extractive distillation column at ascending charge points, and separating said impure propylene oxide therein into a first lighter distillation fraction containing residual methanol and water and substantially all of the propylene oxide, hexenes, hexanes, pentenes and pentanes and oxygen-containing impurities boiling with and above propylene oxide and a first heavier distillation fraction containing oxygen-containing impurities boiling below propylene oxide and substantially all of the extractive distillation agent;

charging a second feedstock comprising said first lighter distillation fraction to a second distillation column and separating it therein into a second partially purified lighter distillation fraction containing pentanes, pentenes and oxygen-containing impurities boiling above propylene oxide, and a second heavier distillation fraction containing substantially all of the propylene oxide, methanol, water, hexenes and hexanes;

separately charging a third feedstock comprising said second heavier distillation fraction and a $C_8$ to $C_{10}$ alkane hydrocarbon extractive distillation agent to a third extractive distillation column at ascending charge points and fractionating them therein into a third lighter distillation fraction containing methanol, water and oxygen-containing impurities boiling above propylene oxide, and a third heavier further purified distillation fraction containing water and substantially all of the propylene oxide, hexenes and hexanes, and extractive distillation agent charged to said third distillation column;

separately charging a fourth feedstock comprising said third heavier distillation fraction and a $C_8$ to $C_{10}$ alkane hydrocarbon extractive distillation agent to a fourth extractive distillation column at ascending charge points and fractionating it therein into a fourth lighter additionally purified distillation fraction consisting essentially of propylene oxide and water and a fourth heavier distillation fraction containing substantially all of the extractive distillation agent, all of the hexenes and hexanes charged to said third distillation column, and also residual quantities of propylene oxide;

separately charging a fifth feedstock comprising said fourth lighter distillation fraction and a $C_2$–$C_6$ alkylene glycol extractive distillation agent to a fifth distillation column at ascending charge points and fractionating it therein into a fifth lighter distillation fraction consisting essentially of propylene oxide and a fifth heavier distillation fraction comprising propylene oxide, water and substantially all of the extractive distillation agent.

6. A distillation process for the purification of a crude propylene oxide feedstock contaminated with impurities including water, propylene, propane, acetaldehyde, methyl formate, propionaldehyde, hexenes, acetone, hexanes, methanol, t-butyl alcohol, pentane, isopentane, pentenes, isopropyl alcohol and t-butyl formate which comprises the steps of:

charging said crude propylene oxide feedstock to a first extractive distillation column;

charging an alkylene glycol extractive distillation agent selected from the group consisting of triethylene glycol and dipropylene glycol to said first extractive distillation column at a feed point above the point of introduction of said impure propylene oxide;

fractionating said crude propylene oxide feedstock in said first extractive distillation column under distillation conditions selected to provide a first lighter distillation fraction containing propylene oxide, propylene, propane, acetaldehyde, methyl formate, hexenes, hexanes, pentenes and pentanes, methanol and water and a first heavier distillation fraction containing substantially all of the propionaldehyde, acetone, t-butyl alcohol, t-butyl formate, isopropyl alcohol, the remainder of the methanol and water and substantially all of the said alkaline glycol extractive distillation agent;

charging a second feedstock comprising said first lighter distillation fraction to a second distillation column;

fractionating said second feedstock in said second distillation column under distillation conditions selected to provide a second lighter distillation fraction containing water, all of the propylene, propane, acetaldehyde, pentanes and pentenes, and a residual amount of propylene oxide, and a second heavier partially purified distillation fraction comprising propylene oxide, water, hexenes and hexanes;

charging a third feedstock comprising said second heavier distillation fraction to a third extractive distillation column;

charging an octane extractive distillation agent to said third extractive distillation column at a feed point above the point of introduction of said third feedstock;

fractionating said third feedstock in said third extractive distillation column under distillation conditions selected to provide a third further purified lighter distillation fraction containing water and substantially all of the acetaldehyde, methyl formate and methanol and residual quantities of propylene oxide and octane extractive distillation agent, and a third heavier distillation fraction containing water, substantially all of the propylene oxide and octane charged to said third distillation column and substantially all of the hexenes and hexanes charged to said third distillation column;

charging a fourth feedstock comprising said third heavier distillation fraction to a fourth extractive distillation column;

charging an octane extractive distillation agent to said fourth extractive distillation column at a feed point above the point of introduction of said fourth feedstock;

fractionating said fourth feedstock in said fourth extractive distillation column under distillation conditions selected to provide a fourth lighter additionally purified distillation fraction consisting essentially of propylene oxide and water and a fourth heavier distillation fraction containing substantially all of the octane extractive distillation agent, hexenes and hexanes charged to said fourth distillation column, and also residual quantities of propylene oxide;

charging a fifth intermediate feedstock comprising said fourth lighter distillation fraction to a fifth extractive distillation column, charging an alkylene glycol extractive distillation agent selected from the group consisting of triethylene glycol and dipropylene glycol to said fifth extractive distillation column at a feed point above the point of introduction of said fifth feedstock;

fractionating said fifth feedstock in said fifth extractive distillation column under extractive distillation conditions selected to provide a fifth lighter distillation fraction consisting essentially of propylene oxide and a fifth heavier distillation fraction comprising water, alkylene glycol extractive distillation agents and residual quantities of propylene oxide, and recycling said fifth heavier distillation fraction to said first distillation column.

7. A method as in claim 6 wherein the pressure maintained at the top of the first distillation column is about 15-25 psia, wherein the temperature maintained at the top of the first distillation column is about 80°-120° F., wherein the pressure maintained at the bottom of the first distillation column is about 20-50 psia, and wherein the temperature maintained at the bottom of the first distillation column is about 300°-400° F.

8. A method as in claim 6 wherein the pressure maintained at the top of the second distillation column is about 35-45 psia, wherein the temperature maintained at the top of the second distillation column is about 110°-130° F., wherein the pressure maintained at the bottom of the second distillation column is about 40-50 psia, and wherein the temperature maintained at the bottom of the second distillation column is about 150°-160° F.

9. A method as in claim 6 wherein the pressure maintained at the top of the third distillation column is about 20-40 psia, wherein the temperature maintained at the top of the third distillation column is about 130°-160° F., wherein the pressure maintained at the bottom of the third distillation column is about 30-50 psia, and wherein the temperature maintained at the bottom of the third distillation column is about 180°-220° F.

10. A method as in claim 6 wherein the pressure maintained at the top of the fourth distillation column is about 10-30 psia, wherein the temperature maintained at the top of the fourth distillation column is about 100°-130° F., wherein the pressure maintained at the bottom of the fourth distillation column is about 25-45 psia, and wherein the temperature maintained at the bottom of the fourth distillation column is about 250°-290° F.

11. A method as in claim 6 wherein the pressure maintained at the top of the fifth distillation column is about 15 to about 25 psia, wherein the temperature maintained at the top of the first distillation column is about 80° to about 120° F., wherein the pressure maintained at the bottom of the first distillation column is about 20 to about 50 psia and wherein the temperature maintained at the bottom of the fifth distillation column is about 180° to about 220° F.

12. A method as in claim 6 wherein the first distillation column contains about 50 to about 80 theoretical trays, wherein the crude propylene oxide feedstock is introduced at least about 10 trays from the bottom of the column, wherein the triethylene glycol or dipropylene glycol extractive distillation agent is introduced at least about 20 theoretical trays above the tray at which the crude propylene oxide feedstock is introduced, and wherein the weight ratio of crude propylene oxide feedstock to the said extractive distillation agent is about 2 to about 7.

13. A method as in claim 6 wherein the second distillation column contains about 20 to about 40 theoretical trays, and wherein the second feedstock is introduced at least about 8 trays from the bottom of the column.

14. A method as in claim 6 wherein the third distillation column contains about 50 to about 90 theoretical trays, wherein the third feedstock is introduced at least about 30 trays from the bottom of the column, wherein the third extractive distillation agent is introduced at least about 10 theoretical trays above the tray at which the third feedstock is introduced, and wherein the ratio of third feedstock to the third extractive distillation agent is about 0.1 to about 0.3.

15. A method as in claim 6 wherein the fourth distillation column contains about 50 to about 90 theoretical trays, wherein the fourth feedstock is introduced at least about 3 trays from the bottom of the column, wherein the fourth extractive distillation agent is introduced at least about 15 theoretical trays above the tray at which the fourth feedstock is introduced, and wherein the ratio of fourth feedstock to the fourth extractive distillation agent is about 1.3 to about 2.2.

16. A method as in claim 6 wherein the fifth distillation column contains about 10 to about 40 theoretical trays, wherein the fourth feedstock is introduced at least about 5 trays from the bottom of the column, wherein the extractive distillation agent is introduced at least about 20 theoretical trays above the tray at which the fourth feedstock is introduced and wherein the ratio of the fifth feedstock to the fifth extractive distillation agent is about 4 to about 6.

17. A method as in claim 6 wherein a sixth feedstock comprising said first heavier distillation fraction is charged to a sixth distillation column wherein:

said sixth feedstock is fractionated under distillation conditions selected to provide a sixth lighter distillation fraction containing substantially all of the propylene oxide, water, acetone, t-butyl alcohol, methanol and isopropyl alcohol charged to the sixth distillation column and a sixth heavier distillation fraction containing substantially all of the alkylene glycol extractive distillation agent charged to the sixth distillation column, and wherein said sixth heavier distillation fraction is recycled to said first and said fifth distillation columns as said alkylene glycol extractive distillation agents, said sixth distillation column containing about 10 to 30 theoretical trays, and the sixth feedstock being introduced at least about three theoretical trays from the bottom of the column.

18. A method as in claim 6 wherein the pressure maintained at the top of the sixth distillation column is about 0.1–1.0 psia, wherein the temperature maintained at the top of the sixth distillation column is about 90°–130° F., wherein the pressure maintained at the bottom of the sixth distillation column is about 0.1–1.1 psia, and wherein the temperature maintained at the bottom of the sixth distillation column is about 300°–400° F.

19. A method as in claim 6 wherein a seventh feedstock comprising said third lighter distillation fraction and said fourth heavier distillation fraction is charged to a seventh distillation column, and wherein said seventh feedstock is fractionated in said seventh distillation column under distillation conditions selected to provide a seventh lighter distillation fraction containing water and substantially all of the acetaldehyde, methyl formate, propylene oxide, hexenes and methanol and a minor portion of the octane extractive distillation agent charged to the seventh distillation column and a seventh heavier distillation fraction containing substantially all of the octane extractive distillation agent charged to the third and fourth distillation columns, and wherein said seventh heavier distillation fraction is recycled to said third and fourth distillation columns as said octane extractive distillation agents.

20. A method as in claim 19 wherein the pressure maintained at the top of the seventh distillation column is about 15–30 psia, wherein the temperature maintained at the top of the seventh distillation column is about 110°–140° F., wherein the pressure maintained at the bottom of the seventh distillation column is about 20–40 psia, wherein the temperature maintained at the bottom of the seventh distillation column is about 200°–300° F.

21. A method as in claim 19 wherein the seventh distillation column contains about 30 to about 50 theoretical trays, and wherein the seventh feedstock is introduced at least about 20 trays from the bottom of the column.

* * * * *